United States Patent [19]

Bird et al.

[11] Patent Number: 4,997,640
[45] Date of Patent: Mar. 5, 1991

[54] ORAL COMPOSITIONS

[75] Inventors: Nigel P. Bird; Geoffrey S. Ingram; Paul I. Riley, all of Bebington; James A. Ritchie, Spital, all of England

[73] Assignee: Chesebrough-Pond's USA Co., Division of Conopco, Inc., Greenwich, Conn.

[21] Appl. No.: 286,596

[22] Filed: Dec. 19, 1988

[30] Foreign Application Priority Data

Dec. 18, 1987 [GB] United Kingdom ............... 8729564

[51] Int. Cl.$^5$ ...................... A61K 7/16; A61K 7/18
[52] U.S. Cl. ...................................... 424/52; 424/49; 424/55
[58] Field of Search .................... 424/49-58

[56] References Cited

U.S. PATENT DOCUMENTS

| 2,470,906 | 7/1946 | Taylor | 167/93 |
| 3,065,139 | 11/1954 | Ericsson | 167/72 |
| 3,691,492 | 10/1969 | Kotzbauer | 424/141 |
| 3,925,543 | 11/1973 | Donahue | 424/52 |
| 4,022,880 | 5/1977 | Vinson et al. | 424/49 |
| 4,100,269 | 7/1978 | Pader | 424/49 |
| 4,144,323 | 3/1979 | Lamberti | 424/54 |
| 4,160,821 | 7/1979 | Sipos | 424/49 |
| 4,213,961 | 3/1978 | Curtis et al. | 424/54 |
| 4,339,432 | 7/1982 | Ritchey et al. | 424/54 |
| 4,525,343 | 6/1985 | Raaf | 424/54 |
| 4,559,224 | 12/1985 | Raaf | 424/49 |
| 4,622,220 | 11/1986 | Frosch | 424/49 |
| 4,656,031 | 4/1987 | Lane et al. | 424/49 |

FOREIGN PATENT DOCUMENTS 0038867 9/1983 European Pat. Off.
72010399 9/1964 Japan .
2080681 12/1982 United Kingdom .

OTHER PUBLICATIONS

Evers et al., CA 83: 84731p (1975), of Swed. 367,319, 27 May 1974.

Primary Examiner—Shep K. Rose
Attorney, Agent, or Firm—Milton L. Honig

[57] ABSTRACT

The disclosure concerns a toothpaste having antimicrobial activity packaged in a closed container comprising water, an ascorbic acid compound consisting of ascorbic acid, an ascorbic acid salt or an ascorbic acid ester and a copper catalyst for the auto-oxidation of the ascorbic acid compound during use of the toothpaste.

6 Claims, No Drawings

ORAL COMPOSITIONS

The invention relates to oral products for promoting the health of the oral cavity. Known oral products of this kind commonly take the form of mouthwashes and toothpastes, also known as dental creams and which include tooth gel compositions. A variety of active agents are known for use in such products such as anticaries agents, e.g. fluoride, and anti-tartar agents, e.g. pyrophosphates. Another well known group of oral health agents are those which inhibit the growth of dental plaque, which is composed of bacteria. The inhibition of the growth of dental plaque and its removal from the teeth through regular toothbrushing is important since dental plaque, apart from being cosmetically undesirable, is a precursor for a number of oral disorders. For example, acid generated within plaque by the bacterial decomposition of sugars can lead to dental caries, and the mineralisation of plaque leads to the formation of tartar. A number of differing agents have been proposed for use in oral compositions for inhibiting the development of dental plaque on the surfaces of the teeth. These agents generally have an antibacterial action. Many cationic antibacterial agents have been suggested such as the bis biguanides of which chlorhexidine is the most well known. Chlorhexidine is a powerful antibacterial agent but suffers from the disadvantage of having a bitter taste and stains the teeth. Many attempts have been made to overcome these drawbacks, especially the staining problem. In U.S. Pat. No. 3,925,543 (Donohue) and U.S. Pat. No. 4,213,961 (Curtis et al) it is suggested that inclusion of ascorbic acid is beneficial as an anti-stain agent.

It is believed that ascorbic acid was first suggested for use in a dentifrice in U.S. Pat No. 2,470,906 (Taylor) as a means of transforming the mucinous coat in the oral cavity so that it is easily removed from, for example, tooth enamel.

It has been proposed in U.S. Pat No. 3,065,139 (Ericsson et al) to include ascorbic acid as part of an antibacterial preparation effective against a number of bacterial species found in the oral cavity. The antibacterial preparation comprises an oxidising agent, particularly sodium percarbonate, a reducing agent being a compound containing an enediol group (—COH:COH—), especially ascorbic acid, and a catalyst, such as copper, for the reduction-oxidation reaction. The patent teaches that since it is the actual oxidation process of the enediol which exert the antimicrobial action, the reacting components must not be brought together in water solution until the time of application, or immediately before this application. However, they can be mixed in the form of water-free pastes such as by using water-free glycerol as a paste base.

The limited duration of the antimicrobial activity of a solution of ascorbic acid containing a catalytic amount of copper is also referred to in U.S. Pat. No. 3,681,492 (Kotzbauer). This reference discloses that the antimicrobial life of such solutions may be lengthened by the use of nitrogeneous compounds which are capable of complexing with the copper to form a complex having a log stability constant within the range 3 to 14.

JP-B-72010399 (Sun Star) published 28 Mar. 1972 discloses a dentifrice mainly comprising calcium secondary phosphate and also containing 0.02 to 0.20% copper chlorophyll and 0.2 to 8 times the amount of copper chlorophyll of ascorbic acid., The decomposition/colour change of copper chlorophyll and the oxidative decomposition/colouration of ascorbic acid is said to be inhibited.

GB-B-2 080 681 (Fahim & Miller) discloses a therapeutic dentifrice comprising a combination of zinc ions and ascorbic acid but there is excluded any component which would induce oxidation in ascorbic acid.

JP-A-63141921 (Kao) published 14 June 1988 discloses a dentifrice containing ascorbic acid, ascorbic acid salt or ascorbic acid ester and a water-soluble zinc salt, such as zinc chloride, zinc sulphate, zinc acetate, zinc lactate or zinc nitrate. The purpose of the zinc salt is to inhibit the formation of brown-coloured decomposition products produced on oxidation of the ascorbic acid.

We have now surprisingly found that relatively stable antimicrobial toothpaste products according to the present invention may be formulated by packing within a closed container a toothpaste composition containing water, an ascorbic acid compound consisting of ascorbic acid, an ascorbic acid salt or an ascorbic acid ester and a copper catalyst for the auto-oxidation of the ascorbic acid compound.

It has furthermore been unexpectedly discovered that the toothpaste products of the present invention are effective for combating anaerobic bacteria. Therefore, the products of the invention are valuable for the control of gingivitis and/or periodontitis since anaerobic bacteria are believed to be implicated in these diseases (Journal of Clinical Periodontology, 1979, 6, 351–382). In practice, of course, during use of the product some of the ascorbic acid will undergo catalysed auto-oxidation and thereby exert an anti-bacterial action against aerobic bacteria.

The ascorbic acid, also known as L ascorbic acid or Vitamin C, or salt or ester thereof, may be present in the product of the invention in an amount of from about 0.05% to about 5%, preferably about 0.5% to about 5% by weight of the product. A mixture of two or more of ascorbic acid, ascorbic acid salt and ascorbic acid ester may of course be used.

Any physiologically acceptable salt of ascorbic acid may be used. Various alkali metal and alkaline earth metal salts are suitable. Other suitable salts are the ammonium salt and those derived from monoethanolamine, diethanolamine, and amino acids such as arginine and lysine.

Suitable ascorbic acid esters are those in which one or more hydroxy groups in the 2-, 3-, 5- and/or 6-positions are fatty acid ester, sulphate or phosphate. Examples are ascorbic acid-2-acetate, ascorbic acid-2-sulphate, ascorbic acid-2-phosphate, ascorbic acid-2-palmitate.

The copper catalyst is preferably incorporated in the product of the invention in the form of a water-soluble copper salt to provide the catalyst in ionic form in the aqueous liquid medium of the toothpaste. Any suitable physiologically acceptable salt may be used. Examples of suitable copper salts are copper sulphate, copper halides and pseudohalides, copper nitrate, copper salts of carboxylic acids in the homologous series formic acid to decanoic acid, copper salts of polybasic acids in the series oxalic acid to suberic acid, and copper salts of hydroxycarboxylic acids including glycolic acid, lactic acid, tartaric acid, malic acid and citric acid.

The copper catalyst may, however, be included in the toothpaste of the invention in the form of copper ions carried or copper compounds precipitated on a solid or colloidal support such as silica, a clay (e.g. montmorillonite) or upon a biopolymer or synthetic polymer. Copper compounds which are substantially insoluble but which nevertheless release sufficient copper ions to be catalytic, such as copper hydrotalcite, may also be used.

It is already known from EP-A-38 867 to incorporate copper compounds in oral compositions as a source of copper ions for the purpose of producing an anti-plaque effect. Various copper compounds are disclosed therein and such compounds may be incorporated in oral compositions according to this invention.

The amount of catalytic copper, calculated as the metal, which may be included in compositions according to the present invention ranges from about 1 ppm to 1000 ppm, preferably 10 to 200 ppm, more preferably 30 to 100 ppm.

The copper catalyst for the auto-oxidation of ascorbic acid may be used combined with other metals such as iron, manganese, nickel, cobalt and vanadium.

From the documents referred to above it is evident that the antibacterial activity of the copper catalysed auto-oxidation of ascorbic acid has been recognised for many years. To be active it appears that the copper must be sufficiently available for it to act as a catalyst. For example, copper which is complexed such as in copper chlorophyll as used in the compositions of JP-B-72010399 (Sun Star) is ineffective as a catalyst. The suitability of a copper compound as catalyst for the auto-oxidation of ascorbic acid and thus its suitability for use in compositions of this invention can readily be checked by determining whether it leads to the rapid removal of dissolved oxygen from an oxygen-containing aqueous solution of ascorbic acid. Such a test, referred to herein as the Oxygen Consumption Test, may be carried out in the following way.

The principle of the test is that, during the copper-catalysed auto-oxidation of ascorbic acid, oxygen is consumed and the rate of loss of oxygen from a closed aqueous ascorbic acid/copper catalyst system can be easily monitored by means of an oxygen electrode. Stock solutions of ascorbic acid (prepared daily at 1.0% w/w) and of the copper catalyst (100ppm Cu) were prepared by dissolving the appropriate material in distilled, oxygen-saturated water. Lower concentrations of copper catalyst were prepared by appropriate dilutions. The distilled water was saturated with oxygen by leaving it overnight in a container open to the atmosphere.

The oxygen electrode was set up in oxygen-saturated distilled water in the electrode cell and the display was adjusted to show an oxygen content of 100 units. The distilled water was removed and rapidly replaced with a mixture of equal volumes of the ascorbic acid solution and the solution of the copper compound in such a way that the dilutions resulted in final concentrations of 0.5% ascorbic acid and 5 ppm copper. A small magnetic follower in the base of the electrode cell ensured rapid mixing of the two solutions.

Rate of loss of oxygen from the solution can be recorded either manually by noting the digital readout of oxygen content or automatically by connecting a chart recorder to the oxygen electrode.

Water-soluble copper salts which result in a rapid consumption of oxygen exhibit catalytic activity. Such salts result in a consumption of at least 50% of the oxygen content of the water in two minutes.

The following table gives data obtained using copper sulphate and copper chlorophyllin, respectively. They show that copper chlorophyllin is not catalytically active.

| Time (mins) | Electrode Reading (% Oxygen) | |
| --- | --- | --- |
| | Copper salt | Copper chlorophyllin |
| 0.5 | 79 | 105 |
| 1.0 | 58 | 101 |
| 2.0 | 26 | 98 |
| 4.0 | 5 | 95 |

A similar procedure can be used to show that copper in substantially insoluble form may be catalytically active. Results for basic copper carbonate precipitated onto silica (Form A) and copper hydrotalcite (Form B) are given below. In these tests 0.1 g of material was combined with 8 ml of 0.5% ascorbic acid solution in oxygen-saturated distilled-water.

| Time (mins) | Electrode Reading (% Oxygen) | |
| --- | --- | --- |
| | Cu in Form A | Cu in Form B |
| 0.5 | 68 | 21 |
| 1.0 | 22 | 12 |
| 2.0 | 7 | 6 |
| 4.0 | 3 | 3 |

In one particular embodiment, the oral composition of the invention also contains an iodide or bromide, particularly an alkali metal iodide or bromide, and preferably potassium iodide. The amount of potassium iodide may be from 0.01 to 2%, such as from 0.1 to 1%, by weight of the composition. Equivalent amounts of other iodides or of bromides may be used. A mixture of an iodide and a bromide may, of course, be employed. The presence of these halides had been found to enhance the antibacterial action obtained on oxidation of the ascorbic acid compound.

In another embodiment of the invention the toothpaste product also includes a source of zinc ions to provide an enhanced therapeutic effect.

The beneficial action of zinc salts is already known. A large number of zinc salts suitable for use in oral compositions are disclosed in U.S. Pat. Nos. 4,100,269, 4,022,880, 4,160,821 and 4,656,031. These include by way of example, zinc citrate, zinc chloride and zinc sulphate. Examples of other zinc salts that have been proposed are zinc carboxymethyloxysuccinate (U.S. Pat. No. 4,144,323), zinc glycinate (U.S. Pat. No. 4,339,432), and zinc aspartate (U.S. Pat. No. 4,622,220).

The amount of the zinc salt used in the oral composition of the invention may be from about 0.05% to about 1.5%, preferably from about 0.1% to about 0.7%, calculated as zinc.

The oral composition of the invention is in the form of a toothpaste, by which term we include products sometimes referred to as dental creams or gels. Toothpaste usually comprises a suspension of a particulate solid abrasive cleaning agent in a thickened aqueous humectant liquid.

In the oral composition of this invention various of the known abrasive cleaning agents can be used but silica abrasives are preferred. A number of forms of silica are already known in the art as being suitable for dentifrice use including silica xerogels, precipitated silicas and crystalline silicas. Such silicas are referred to in U.S. Pat. No. 3,538,230 and GB-A-2 167 956. Other compatible abrasives include water-insoluble sodium metaphosphate, alumina, calcium pyrophosphate and plastics materials. Alumina abrasives include the hydrated aluminas. A conventional level of abrasive ranging from 5 to 75% by weight of the toothpaste may be used. As is well know, use of various silica abrasives permits the toothpaste to be formulated in the form of a transparent or translucent gel product.

Humectants which may be used include glycerol, sorbitol syrup, polyethylene glycol, lactitol, xylitol or hydrogentated corn syrup. The total amount of humectant present will generally range from 10% to 85% by weight of the toothpaste, more usually 20% to 60%.

The remaining liquid phase of toothpaste according to the invention mainly comprises water which will usually amount to from about 5% to about 45% by weight of the toothpaste. The amount of water in the toothpaste, including any present in the humectant, will generally be in the range about 5% to about 60%, such as from about 10% to about 55% by weight of the toothpaste.

Numerous binding or thickening agents have been indicated for use in toothpastes, preferred ones being hydroxymethylcellulose, sodium carboxymethylcellulose and xanthan gum. Others include natural gum binders such as gum tragacanth, gum karaya and gum arabic, Irish moss alginates and carrageenans. Silica thickening agents include the silica aerogels and various precipitated silicas. Mixtures of binders and thickening agents may be used. The amount of binder and thickening agent included in a toothpaste is generally between 0.1 to 10% by weight.

Toothpastes generally also comprise a surfactant. Commonly used is sodium lauryl sulphate but others are also known to be suitable. The amount of surfactant is usually within the range 0.5 to 5% by weight of the composition.

A variety of other known toothpaste ingredients may also be included in toothpastes formulated in accordance with the present invention. Such ingredients include an anti-caries ingredient such as sodium fluoride or sodium monofluorophosphate or other effective fluorine-containing compound; an additional anti-plaque agent such as an antimicrobial compound for example chlorhexidine or 2,4,4′-trichloro-2′hydroxy-diphenyl ether; sweetening agent such as saccharin; an opacifying agent such as titanium dioxide; a preservative such as formalin; a flavouring agent such as peppermint oil or spearmint oil; a colouring agent; or pH controlling agent such as an acid, base or buffer, for example benzoic acid, to give a pH of from about 4 to about 8, preferably about 5 to about 7. In order to minimise any slight surface discolouration of an extruded toothpaste ribbon lower pHs are preferable such as about 4 to about 5.

Preferred oral compositions of this invention contain 500–5000 ppm F, preferably 1000–2500 ppm F, as ionic fluoride or monofluorophosphate.

For a further discussion of the formulation of toothpastes reference is made to Harry's Cosmeticology, Seventh Edition 1982, Edited by J B Wilkinson and R J Moore, pages 609 to 617.

The toothpaste of the invention is packed with a suitable closed container using conventional procedures. Such containers include a toothpaste tube, commonly constructed of aluminium or a laminated plastic material, a pump dispenser or an aerosol can.

As is apparent from the documents referred to above the antibacterial activity of the copper catalysed auto-oxidation of ascorbic acid has been recognised for many years. Previous studies have concluded that bacterial inhibition was due to hydrogen peroxide formed during the auto-oxidation of ascorbic acid (see J. Bacteriol. 68, 622–626, 1954).

In the study reported below combinations of copper and ascorbic acid have been tested under strict anaerobic conditions. Under these conditions no oxygen would be present to enable auto-oxidation of the ascorbic acid reaction sequence to reach completion and no hydrogen peroxide would be formed.

Areas of anaerobiosis are encountered in both supra and sub-gingival plaque from where large numbers of obligate anaerobic bacteria can be isolated. Microbiological and immunological evidence has implicated anaerobic bacteria in the etiology of periodontal diseases.

Test Procedure

1. A medium based on that developed by Socransky et al (J. Clin. Microbiol, 22, 2, 303–305) was used because of its low residual copper content. L-ascorbic acid was added to give a final concentration of 0.3 and 0.5% and the pH was adjusted to 6.8 using 1N sodium hydroxide. The medium was dispensed into 4.8 ml volumes and was reduced by placing in an anaerobic environment.

2. Bacterial cell suspensions were prepared from colonies growing anaerobically on supplemented blood agar (see Anaerobe Laboratory Manual 4th Edition, p 144, 1977, by Holdeman et al) emulsified in a small volume of distilled water. Final cell density was adjusted to approximately 1.0 at 570 nm.

3. 100 μl cell suspension was used to inoculate the medium containing ascorbic acid and then 30–100 μl of a stock solution of copper sulphate ($CuSO_4.5H_2O$) was added to give final concentrations of 15, 30 and 50 μg/ml copper. The test systems were mixed by inversion and then incubated until growth was recorded in corresponding control broths.

4. Minimum inhibitory concentration was determined as the lowest concentration of copper/ascorbic acid which prevented visible growth.

5. An aliquot from broths was plated onto supplemented blood agar to confirm that cells were dead. Plates were incubated until growth was obtained on corresponding controls.

Steps 2–5 were all performed in an anaerobic cabinet under an environment of 10% hydrogen, 10% carbon dioxide and 80% nitrogen. Medium, test solutions and equipment were sterilised by autoclaving. The results are given in the following table.

| Strain Reference | % Ascorbic Acid: | | | | | |
|---|---|---|---|---|---|---|
| | 0.3 | | | 0.5 | | |
| | μg/ml copper | | | | | |
| | 15 | 30 | 50 | 15 | 30 | 50 |
| Streptococcus sanguis 200 | + | + | − | + | + | − |
| Streptococcus sanguis 201 | + | + | + | + | + | − |
| Streptococcus sanguis 204 | + | + | − | + | + | − |
| Streptococcus sanguis 205 | + | + | − | + | − | − |
| Streptococcus mutans M1 | + | + | − | + | + | − |
| Actinomyces naeslundii A3 | + | + | − | + | − | − |
| Actinomyces naeslundii 422 | + | + | − | + | − | − |
| Actinomyces viscosus A1 | + | + | − | + | − | − |

-continued

| Strain Reference | % Ascorbic Acid: | | | | | |
|---|---|---|---|---|---|---|
| | 0.3 | | | 0.5 | | |
| | μg/ml copper | | | | | |
| | 15 | 30 | 50 | 15 | 30 | 50 |
| Bacteroides melaninogenicus 1 | + | − | − | + | − | − |

+ = turbid growth
− = no obvious growth

A corresponding control containing no copper and no ascorbic acid showed growth. In the presence of 0.3% ascorbic acid some but not all the strains were inhibited by 50 μg/ml copper. In 0.5% ascorbic acid half strains were inhibited by 30 μg/ml copper and all strains tested were inhibited by 50 μg/ml copper. One broth showing no obvious growth of each strain was tested to confirm cell death, in all cases no viable cells were recovered. The growth of the obligate anaerobe *Bacteroides melaninogenicus* confirmed that anaerobic conditions were maintained during the test.

In tests utilising the same growth medium but carried out under aerobic conditions similar results were obtained. In these further tests it was determined that the minimum inhibitory concentration for copper alone was above 100 ppm and between 100 and 150 ppm, and for ascorbic acid alone the minimum inhibitory concentration was above 1%, being between 1% and 2%.

The present invention therefore in a further aspect relates to the use of compositions comprising effective amounts of copper and ascorbic acid for inhibiting the growth of anaerobic bacteria in the oral cavity, and to the use of copper and ascorbic acid for the manufacture of stable toothpaste oral compositions for combating anaerobic bacteria in the oral cavity.

The following examples illustrate the invention. Percentages are by weight.

EXAMPLE 1

A toothpaste was made having the following composition.

| Ingredient | % |
|---|---|
| Abrasive silica | 10.00 |
| Thickening silica | 8.00 |
| Sorbitol syrup (70% solution) | 40.50 |
| Xanthan gum | 1.00 |
| Sodium lauryl sulphate | 1.50 |
| Sodium monofluorophosphate | 0.82 |
| Titanium dioxide | 1.00 |
| Ascorbic acid | 2.00 |
| Copper sulphate pentahydrate | 0.019* |
| Saccharin | 0.20 |
| Flavour | 1.00 |
| Water | to 100.00 |

*corresponds to about 50 ppm Cu.

The toothpaste is made using conventional procedures and conventional toothpastes mixers. The copper sulphate is added early in the process with other water-soluble ingredients such as saccharin and sodium monofluorophosphate. The ascorbic acid is added as a solution in water, adjusted to pH 5 with sodium hydroxide, after the detergent and prior to the flavour in the final stages of the process. As in conventional processes, all mixing is carried out under vacuum. Finally the toothpaste is filled into plastic laminate tubes using standard filling equipment within 24 hours of manufacture and the tubes closed by heat sealing in the usual way.

In an in vitro plaque test the above toothpaste was shown to inhibit the formation of dental plaque. The test was performed on the toothpaste just after it had been prepared and also two weeks later when a similar level of plaque inhibition was obtained indicating that the paste had not lost activity over time. This result is consistent with the finding that the ascorbic acid in the above toothpaste is stable in spite of the presence of copper. Analysis for ascorbic acid after 4 months storage at ambient temperature gave a value of 1.9% by iodine titration whereas the nominal level was 2.0%.

Even after 5 months storage of the toothpaste the copper was still active to catalyse the auto-oxidation of the ascorbic acid. This was shown by using a slurry of the toothpaste in the oxygen consumption test described above. In this case one part by weight of the toothpaste was slurried with 6 parts by weight of oxygen-saturated distilled water. A comparative experiment was also carried out using a placebo paste containing no ascorbic acid and no copper. The results were as follows.

| | Electrode Reading (% Oxygen) | |
|---|---|---|
| Time (mins) | Toothpaste of Invention Aged 5 months | Placebo |
| 1.0 | 66 | 90 |
| 2.0 | 42 | 80 |
| 4.0 | 9 | — |
| 10.0 | 3 | 71 |

EXAMPLE 2

A toothpaste was made having the following composition.

| Ingredient | % |
|---|---|
| Silica xerogel | 10.0 |
| Silica aerogel | 8.0 |
| Sorbitol syrup (70% solution) | 40.0 |
| Xanthan gum | 1.0 |
| Sodium lauryl sulphate | 1.5 |
| Zinc citrate trihydrate | 0.5 |
| Ascorbic acid | 2.0 |
| Copper sulphate pentahydrate | 0.0038* |
| Potassium iodide | 1.0 |
| Sodium monofluorophosphate | 1.12 |
| Sodium saccharin | 0.2 |
| Titanium dioxide | 1.0 |
| Flavour | 1.0 |
| Water | to 100.00 |

*correspond to about 10 ppm Cu.

The toothpaste was manufactured and filled into a container and the container then closed in the manner described in Example 1.

What we claim is:

1. A toothpaste having anti-anaerobic bacterial activity packaged within a closed container, the toothpaste containing from about 5% to about 60% by weight of water, from about 0.05% to about 5% by weight of an ascorbic acid compound selected from the group consisting of ascorbic acid, an ascorbic acid salt and an asorbic acid ester, from 500 to 5000 ppm fluoride, and from 1 to 1000 ppm of a copper catalyst for the auto-oxidation of the ascorbic acid compound selected from the group consisting of copper sulphate, copper halides, copper pseudohalides, copper nitrate, copper hydrotalcite, copper salts of polybasic acids in the series oxalic acid to suberic acid, copper salts of carboxylic acids in the homologous series formic acid to decanoic acid, and copper salts of glycolic acid, tartaric acid, malic acid and citric acid.

2. A toothpaste as claimed in claim 1 wherein the copper catalyst is present in the toothpaste in the form of a water-soluble copper salt.

3. A toothpaste as claimed in claim 1 wherein the amount of copper is 10 to 200 ppm.

4. A toothpaste as claimed in claim 3 wherein the amount of copper is 30 to 100 ppm.

5. A toothpaste as claimed in claim 1 wherein the amount of the ascorbic acid compound is present in an amount of from about 0.5% to about 5% by weight of the toothpaste.

6. Method of inhibiting the growth of anaerobic bacteria in the oral cavity which comprises treating the oral cavity with a composition in accordance with claim 1.

* * * * *